(12) United States Patent
Tsui et al.

(10) Patent No.: US 9,395,364 B2
(45) Date of Patent: Jul. 19, 2016

(54) BIOMARKERS FOR INFLAMMATORY BOWEL DISEASE WITH ANKYLOSING SPONDYLITIS

(71) Applicant: UNIVERSITY HEALTH NETWORK, Toronto (CA)

(72) Inventors: Florence Wing Ling Tsui, Oakville (CA); Robert Davies Inman, Toronto (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 0 days.

(21) Appl. No.: 14/764,492

(22) PCT Filed: Jan. 17, 2014

(86) PCT No.: PCT/CA2014/000033
§ 371 (c)(1),
(2) Date: Jul. 29, 2015

(87) PCT Pub. No.: WO2014/117250
PCT Pub. Date: Aug. 7, 2014

(65) Prior Publication Data
US 2016/0061832 A1    Mar. 3, 2016

Related U.S. Application Data

(60) Provisional application No. 61/758,940, filed on Jan. 31, 2013.

(51) Int. Cl.
G01N 33/53 (2006.01)
G01N 33/564 (2006.01)
G06F 19/00 (2011.01)

(52) U.S. Cl.
CPC .......... *G01N 33/564* (2013.01); *G06F 19/3431* (2013.01); *G01N 2333/4703* (2013.01); *G01N 2333/4704* (2013.01); *G01N 2800/065* (2013.01); *G01N 2800/52* (2013.01)

(58) Field of Classification Search
None
See application file for complete search history.

(56) References Cited

FOREIGN PATENT DOCUMENTS

WO    WO 2013/010254    1/2013

OTHER PUBLICATIONS

Canalis et al., "Bone morphogenic proteins, their antagonists, and the skeleton", *Endocrine Reviews* 24(2):218-235, 2003.
International Preliminary Report on Patentability for PCT/CA2014/000033, mailed Aug. 4, 2015.
International Search Report for PCT/CA2014/000033, mailed May 5, 2014.
Rudwaleit et al., "Ankylosing spondylitis and bowel disease", *Best Practice & Research Clinical Rheumatology* 20(3):451-471, 2006.
Tsui et al., "Serum levels of novel noggin and sclerostin-immune complexes are elevated in ankylosing spondylitis", *Annals of the Rheumatic Diseases* 73:1873-1879, 2014.

*Primary Examiner* — Jacob Cheu
(74) *Attorney, Agent, or Firm* — Norton Rose Fulbright US LLP

(57) ABSTRACT

There is provided herein a method for categorizing a patient having inflammatory bowel disease as being at risk for developing ankylosing spondylitis. The method comprises the use of a patient level of auto-antibodies directed against noggin (NOG) and/or sclerostin (SOST) to determine a risk for the patient developing ankylosing spondylitis. There is also provided methods of monitoring ankylosing spondylitis treatment using these auto-antibodies.

11 Claims, 11 Drawing Sheets

Fig. 2

Epitope spreading →  Molecular mimicry

| | 54 | 77 | |
|---|---|---|---|
| NOG | PDPIFDEKEKDLNETLLRSLLGGHYDPGFMAISPPEDRPGGGGG | | (SEQ. ID NO. 9) |
| Mycobacterium (glycosyl hydrolase) | | MtTiPPEDiPG | (SEQ. ID NO. 10) |
| Akkermansia muciniphila (glycosyl transferase) | | PPEDRPG | (SEQ. ID NO. 11) |
| Klebsiella (EefX protein) | | SPPEDRrG | (SEQ. ID NO. 12) |

BIOMARKERS FOR INFLAMMATORY BOWEL DISEASE WITH ANKYLOSING SPONDYLITIS

RELATED APPLICATIONS

This application is a national phase application under 35 U.S.C. §371 of International Application No. PCT/CA2014/000033 filed Jan. 17, 2014, which claims priority to U.S. Provisional Application No. 61/758,940 filed on Jan. 31, 2013. The entire contents of each of the above-referenced disclosures is incorporated herein by reference without disclaimer.

FIELD OF THE INVENTION

The invention relates to Inflammatory Bowel Disease and Ankylosing Spondylitis, and more particularly to biomarkers therefor.

BACKGROUND OF THE INVENTION

Inflammatory bowel disease (IBD) is a complex inflammatory gastrointestinal (GI) disease involving multiple environmental and genetic risk factors. There are two main entities: Crohn's disease (CD) and ulcerative colitis (UC). Originally being considered as a disease of industrialized countries, IBD is now an emerging global disease as its prevalence is on the rise, in both children and adults, even in developing countries. There remains regional difference in its prevalence; with Europe and North America having the highest prevalence rates. Europe has the highest annual incidence of UC (24.3 per 100,000 person-years) and North American has the highest annual incidence of CD (20.2 per 100,000 person-years). In Europe and North American, there are approximately 3.6 million IBD patients suffering from this devastating chronic disease. In 2012, there are about 233,000 Canadians with IBD, and the estimated cost (including medical costs, indirect costs and long-term work losses) is about $2.8 billion. IBD patients suffer significant abdominal pain, recurrent diarrhea and some have severe complications such as colon cancer, sclerosing cholangitis, abscess, fistula formation and pouchitis. Thus, these patients encounter numerous challenges including poor quality of life, expensive medications, employment problems and lack of appropriate support. IBD patients have higher mortality rates compared to the general population.

Ankylosing spondylitis (AS) is a chronic and disabling spinal disease affecting predominantly young men. It is also a complex disease involving multiple risk factors. Genetics, environmental and other factors such as epi-genetics play a role in increasing the odds to developing the AS disease. The hallmark of AS is inflammation and ankylosis (fusion of joints) mainly at the cartilage/bone interface including the enthesis (where ligaments or tendons attach to bone). It can lead to significant spinal disease and peripheral arthritis. The current view considers new bone formation at the enthesis as a pathological response to injury and that joint inflammation precedes ossification. Early stages of ankylosis involve squaring of the vertebral bodies and formation of syndesmophytes. Total spinal ankylosis ("Bamboo spine") is commonly found in the most severe cases. The cause of chronic joint inflammation is not known. There is an ongoing debate on whether chronic inflammation and new bone formation are linked events or independent processes. In North America, the prevalence of AS is about 1 in 200. Currently, there are about 200,000 Canadians with AS.

AS is usually diagnosed according to the modified New York criteria which include a combination of clinical features such as limited motion of the lumbar spine, persistent lower back pain, limited chest expansion; and radiographic evidence of sacroiliitis. Although joint inflammation can be detected early in the disease process (at least within the first year of symptom onset) using magnetic resonance imaging (MRI) technology, it is not a definitive diagnosis test for AS. The subsequent spinal structural changes as visualized on radiographs appear relatively late. This likely explains why it can take 5-10 years to confirm a diagnosis of AS after the initial onset of disease symptoms. Currently, monitoring of patient outcomes in AS relies on the detection of radiographic changes which represent irreversible structural damage. Radiographic changes of the spine (cervical and lumbar) in AS patients are scored using the modified Stoke AS Spine Score (mSASSS).

In summary, severe cases of both chronic diseases (IBD and AS) are extremely disabling and require life-time medical treatments. The availability of biomarkers could not only facilitate rapid diagnosis, but could also provide better assessment and improved ability to determine prognosis. 15-40% of IBD patients have extra-intestinal manifestations such as uveitis, primary sclerosing cholangitis and axial arthritis. Articular manifestations are the most common, affecting about 30% of IBD patients. Isolated sacroiliitis was detected on pelvic X-rays of 2-18% and on CT scans of 14-33% IBD patients respectively. Conversely, one of the extra-articular manifestations of ankylosing spondylitis (AS) is IBD, with 5-10% of AS patients having concomitant IBD. About 60% of AS patients have microscopic colitis identified by colonoscopy. Symptoms of AS can precede IBD symptoms in 31-50% of patients. In 15-40% of cases, both IBD and AS symptoms can occur simultaneously. In patients with concomitant IBD and AS, 39% had IBD symptoms before having AS symptoms, 52% had AS symptoms first and 9% had concurrent IBD and AS symptoms.

Biologic response modifiers (such as Tumor Necrosis Factor inhibitors [TNFi]) are effective in both CD and AS, implicating both diseases share common pathological pathways. However, not all CD/AS patients respond to this treatment. In CD, independent predictors of good response include shorter disease duration, younger age, high CRP, and isolated colitis, while isolated ileitis, strictures and smoking are associated with poor response to TNFi. In AS, shorter disease duration is a strong predictor of treatment response. Other clinical parameters associated with better response to TNFi in AS patients includes younger age, increased acute phase proteins, better functional status, male gender, and significant inflammation detected by MRI. We reported recently that in AS patient treated with TNFi, a combination of biomarkers could better predict treatment response than using acute phase proteins alone. Yet none of these parameters, even when used in combinations, have sufficient sensitivity and specificity to provide a personalized and optimal management of the disease. It is clear that a better understanding of the pathogenesis of these diseases is essential to facilitate accurate predictions of responders and identification of patients likely to develop adverse effects. Treatments with biologics (such as TNFi) are expensive and associated with a significant side effect profile including increased risk of infections and malignancies. Hence, it is imperative to identify biomarkers to screen patients who are likely to benefit from this treatment and in addition to monitor their response to treatment in a timely manner in order to avoid potential serious adverse effects.

Genetics plays a key role in both IBD and AS. While only 8% of Caucasians are HLA-B27 positive, both primary AS and IBD-related AS are associated with B27 positivity. The association is much stronger in AS patients (more than 90%) than in patients with both AS and IBD (25-78%). Recent genetic analyses on complex diseases using genome-wide association (GWA) studies have been extremely successful in revealing IBD susceptibility loci, in particular those that are shared with other inflammatory diseases such as AS. The most recent estimate includes 163 IBD loci, and about 28 of them were shared between CD and UC. The recent immunochip study identified 12 and 11 AS loci shared with CD and UC respectively. A major achievement of these genetic studies relates to the identification of important biological pathways likely lead to shared pathogenesis in IBD and AS. The most notable non-MHC susceptibility loci shared between CD and AS are ERAP2 and IL23R, implicating common pathways in antigen presentation and adaptive immunity respectively.

AS and IBD patients share similar intestinal inflammation based on histopathological findings. Recent ileocolonoscopy studies suggested that AS and CD patients shared indistinguishable gut histopathology even in the absence of GI symptoms in some AS patients. The importance of IL23 pathway as implicated by genetic studies is reiterated by the finding that comparable IL23 production was detected in the guts of CD and AS patients. The link between gut and joint inflammation suggests a common etiology between IBD and AS, but its origin and underlying pathophysiology remain largely unclear. Better understanding of the pathological basis for the coexistence of AS and IBD would impact on improved management of these patients.

Despite these recent advances, there are currently no biomarkers that can predict the occurrence of ankylosis in IBD, or GI symptoms in AS.

Numerous studies have reported dysbioses/imbalance in the gut microbiome of IBD patients, and these dysbioses are associated with alterations in microbial metabolic functions which could impact on the gut of the host. In these patients, there is decreased bacterial biodiversity. Specific features of CD-associated dysbioses include altered proportion of the Clostridia bacteria, and a significant increase in *Enterobacteria* (specifically *Escherichia/Shigella*: bacteria implicated in gut inflammation). Treatments for IBD were associated with changes of gut microbiome, implicating gut microbiome likely causes IBD. For example, the use of a bowel-specific aminosalicylate drug (5-aminosalicylic acid) was linked to a significant reduction of *Escherichia/Shigella*. Aside from studies implicating that affected ileum in CD patients likely provides a favorable environment for the establishment of pathological *E. coli*, CD patients are susceptible to *Clostridium difficile* infections. Gut-resident microbial antigens are candidates for triggering and sustaining chronic inflammation, leading to changes in the host immune responses.

It is less clear whether AS patients have distinct gut microbiome. For decades, a relationship between reactive arthritis (ReA) and certain *enterobacteria* (e.g. *Salmonella, Yersinia, Shigella* and *Klebsiella*) has been noted. Some ReA patients eventually develop AS. The evidence for the association between AS and bacterial infections remains unresolved, though *Klebsiella* was found to colonize in the guts of AS patients.

In sera of CD and UC patients, numerous signature antibodies have been detected. These include anti-neutrophil cytoplasmic antibodies and antimicrobial antibodies. Representative antimicrobial antibodies are anti-*Saccharomyces cerevisiae* mannan (ASCAs) antibodies, antibodies recognizing *Escherichia coli* outer membrane porin C (OmpC) and the flagellin CBir1. A recent study showed that a combination of these antibodies can predict development of IBD years before diagnosis. However, these serological markers appear to persist during the disease process, even after treatments.

For decades, AS has been viewed as a seronegative disease; distinctive for lacking autoantibodies which represent the hallmarks of autoimmune rheumative diseases such as rheumatoid arthritis and lupus. There has been a recent report of autoantibodies recognizing skeletal/connective tissue antigens in AS, but the relevance of these autoantibodies to AS pathogenesis remains unclear.

In WO 2013/010254, Applicant demonstrated that AS is characterized by elevated levels of autoantibodies (IgGs) against noggin (NOG) and sclerostin (SOST), but they exist mainly as immune complexes (ICs), implicating their role in structural damages. In sera, these ICs exist in a setting of antigen excess, thus accounting for previous difficulties in the identification of these autoantibodies. Elevated levels of NOG/SOST-IgG ICs are disease specific as normal levels of these ICs were found in individuals with mechanical back pain (MBP; the control group for ankylosis) and in IBD patients with no articular manifestations (the control group for inflammation).

NOG-SOST complexes with no antagonistic functions for both BMP and β-catenin signaling were identified from a rat osteosarcoma cell line, but their interacting sites have remained unknown. We have identified not only the sites whereby the two proteins bind, but also formation of ICs involving autoantibodies against NOG and SOST at their interacting sites (NOG-N54 and SOST-S146-specific IgG). This raised the intriguing possibility that these ICs may mimic the inhibitory interaction that naturally occurs between these two proteins and amplify the process. It is likely that the relative abundance of these epitope-specific ICs could fine-tune differential signaling of two different pathways influencing bone homeostasis (BMP and wnt/β-catenin). Our finding that AS patients have higher levels of these autoabs suggests that over-abundance of these autoantibodies would lead to reduced levels of functional NOG and SOST, resulting in enhanced BMP and β-catenin signaling. Neo-ossification would thus be promoted, ultimately leading to spinal ankylosis. The possibility that the NOG- and SOST-specific antibodies interfere with their antagonistic functions in bone formation suggests a specific link between autoimmunity and ankylosis in AS.

SUMMARY OF THE INVENTION

In an aspect, there is provided a method for categorizing a patient having inflammatory bowel disease as being at risk for developing ankylosing spondylitis, the method comprising: a. identifying a patient as having inflammatory bowel disease; b. determining a patient level of auto-antibodies directed against noggin (NOG) and/or sclerostin (SOST) in the patient; c. comparing said level to a control level representing normal individuals; and d. determining that the patient is at risk for developing ankylosing spondylitis if the patient level is higher than the control level.

In an aspect, there is provided a method of selecting treatment for a patient having inflammatory bowel disease; the method comprising the methods described herein for categorizing a patient having inflammatory bowel disease as being at risk for developing ankylosing spondylitis, further comprising selecting a treatment consistent with the treatment of both ankylosing spondylitis and inflammatory bowel disease, if the patient level of the auto-antibodies is higher than the control level.

In an aspect, there is provided a method for categorizing a patient having ankylosing spondylitis as being at risk for developing inflammatory bowel disease, the method comprising: a. identifying a patient as having ankylosing spondylitis; b. determining a patient level of auto-antibodies directed against noggin (NOG) and/or sclerostin (SOST) in the patient; c. comparing said level to a control level representing normal individuals; d. determining that the patient is at risk for developing inflammatory bowel disease if the patient level is higher than the control level.

In an aspect, there is provided a method of determining the severity of ankylosing spondylitis in a patient not being treated for inflammatory bowel disease, comprising: a. determining a patient level of auto-antibodies directed against noggin (NOG) and/or sclerostin (SOST) in the patient; b. comparing said level to a control level representing normal individuals; c. determining the severity of ankylosing spondylitis, wherein the severity is related patient levels of the autoantibodies.

In an aspect, there is provided a method for monitoring treatment in a patient receiving treatment for ankylosing spondylitis, the method comprising: a. determining a patient level of auto-antibodies directed against noggin (NOG) and/or sclerostin (SOST) in the patient; b. comparing said level to a control level representing normal individuals; c. identifying a patient as being non-responsive to treatment if the patient level of auto-antibodies is higher than the control level and prior to treatment and does not decrease following or during treatment; wherein the auto-antibodies are directed against either at least part of a region comprising amino acids 73-102 of NOG or at least part of a region comprising amino acids 95-110 of SOST.

In an aspect, there is provided a method, performed by at least one computing device, for categorizing a patient having inflammatory bowel disease as being at risk for developing ankylosing spondylitis, the method comprising: a. determining, at a processor, a patient as having inflammatory bowel disease; b. determining, at a processor, a patient level of auto-antibodies directed against noggin (NOG) and/or sclerostin (SOST) in the patient; b. determining, at a processor, a control level representing normal individuals; c. determining, at a processor, whether the patient level is higher than the control level; d. determining, at a processor, that the patient is at risk for developing ankylosing spondylitis if the patient level is higher than the control level.

In an aspect, there is provided a system for categorizing a patient having inflammatory bowel disease as being at risk for developing ankylosing spondylitis, the system comprising: a non-transitory computer readable storage medium that stores computer-readable code; a processor operatively coupled to the non-transitory computer readable storage medium, the processor configured to implement the computer-readable code, the computer-readable code configured to: a. identify a patient as having inflammatory bowel disease; b. determine a patient level of auto-antibodies directed against noggin (NOG) and/or sclerostin (SOST) in the patient; c. compare said level to a control level representing normal individuals; d. determine that the patient is at risk for developing ankylosing spondylitis or inflammatory bowel disease if the patient level is higher than the control level.

In an aspect, there is provided a computer program product for use in conjunction with a computer having a processor and a memory connected to the processor, the computer program product comprising a computer readable storage medium having a computer mechanism encoded thereon, wherein the computer program mechanism may be loaded into the memory of the computer and cause the computer to carry out the methods described herein.

BRIEF DESCRIPTION OF FIGURES

These and other features of the preferred embodiments of the invention will become more apparent in the following detailed description in which reference is made to the appended drawings, for which a brief description follows.

FIG. 2. Comparison of NOG-N77 (graph on the left) or NOG-N54 (graph on the right) IgG IC levels in patients with AS alone (n=17), AS-CD (n=7), CD (n=10) and UC (n=10). Results were expressed as arbitrary units relative to the standard AS IgG in the total amount of IgG from 1 ml of each serum sample. 6 out of 10 CD patients (circled in blue) had higher than normal levels of NOG-N77 IgG ICs. However, all CD patients (circled in red) had normal levels of NOG-N54 IgG ICs.

* and ** denote significant p values between groups.

Figure 7:
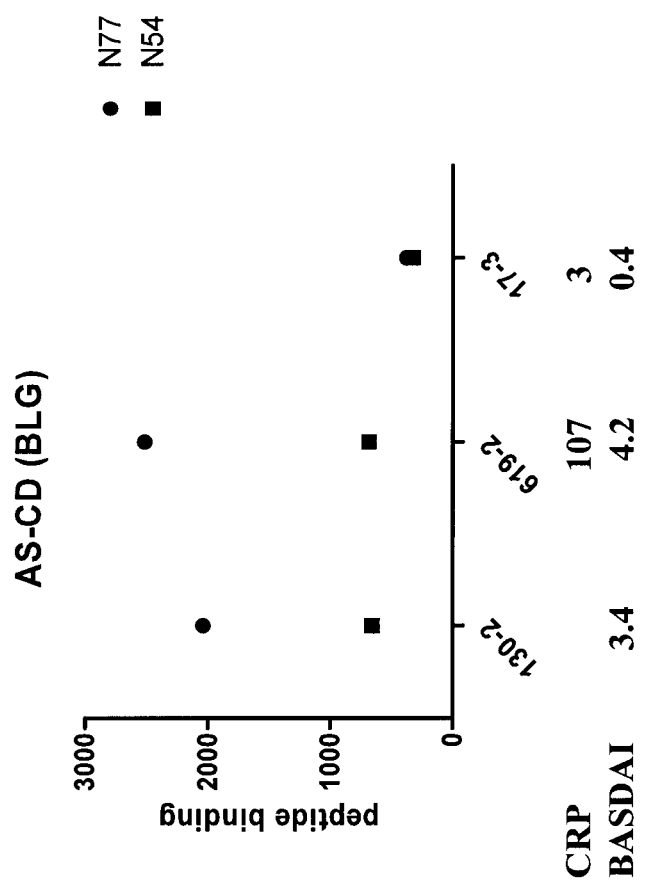

FIG. 7. Correlation of NOG-N77 and -N54 IgG IC levels with CRP and BASDAI in three BLG (biologics) treated AS-CD patients. Sera were obtained from two patients (619-2 and 17-3) who have been treated with BLG for one and two year respectively. 130-2 is a serum sample from a patient who has been treated with BLG for three years. Results were expressed as arbitrary units relative to the standard AS IgG in the total amount of IgG from 1 ml of each serum sample. CRP denotes C-reactive protein and BASDAI denotes Bath Ankylosing Spondylitis Disease Activity Index.

Figure 8:
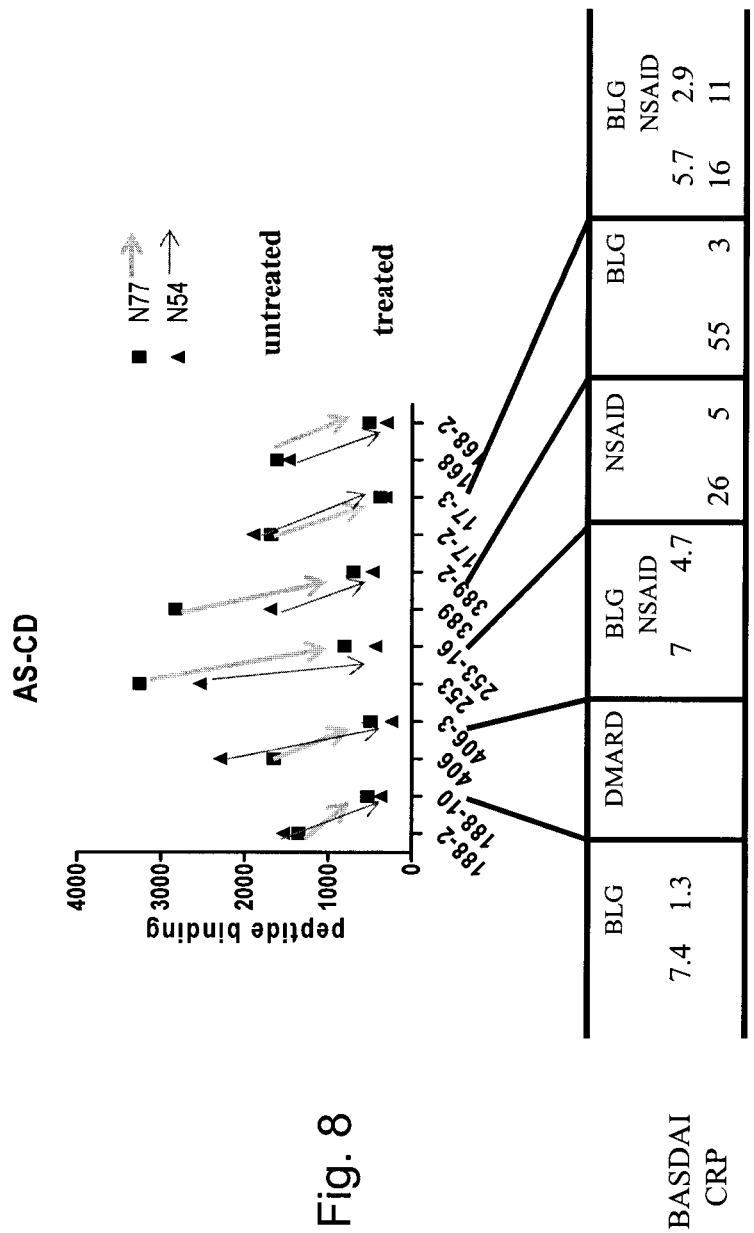

FIG. 8. Comparison of NOG-IgG ICs levels in sequentially obtained serum samples from the same patient before and after treatment. Changes in NOG-N77 and NOG-N54 IgG ICs levels are shown in green and red arrows respectively. Results were expressed as arbitrary units relative to the standard AS IgG in the total amount of IgG from 1 ml of each serum sample. Types of treatment are indicated below the graph. When available, two clinical parameters (BASDAI and CRP) are also indicated. BASDAI denotes Bath Ankylosing Spondylitis Disease Activity Index; CRP denotes C-reactive protein; BLG denotes biologics; DMARD denotes Disease-modifying anti-rheumatic drugs; NSAID denotes non-steroidal anti-inflammatory drugs.

Figure 9:
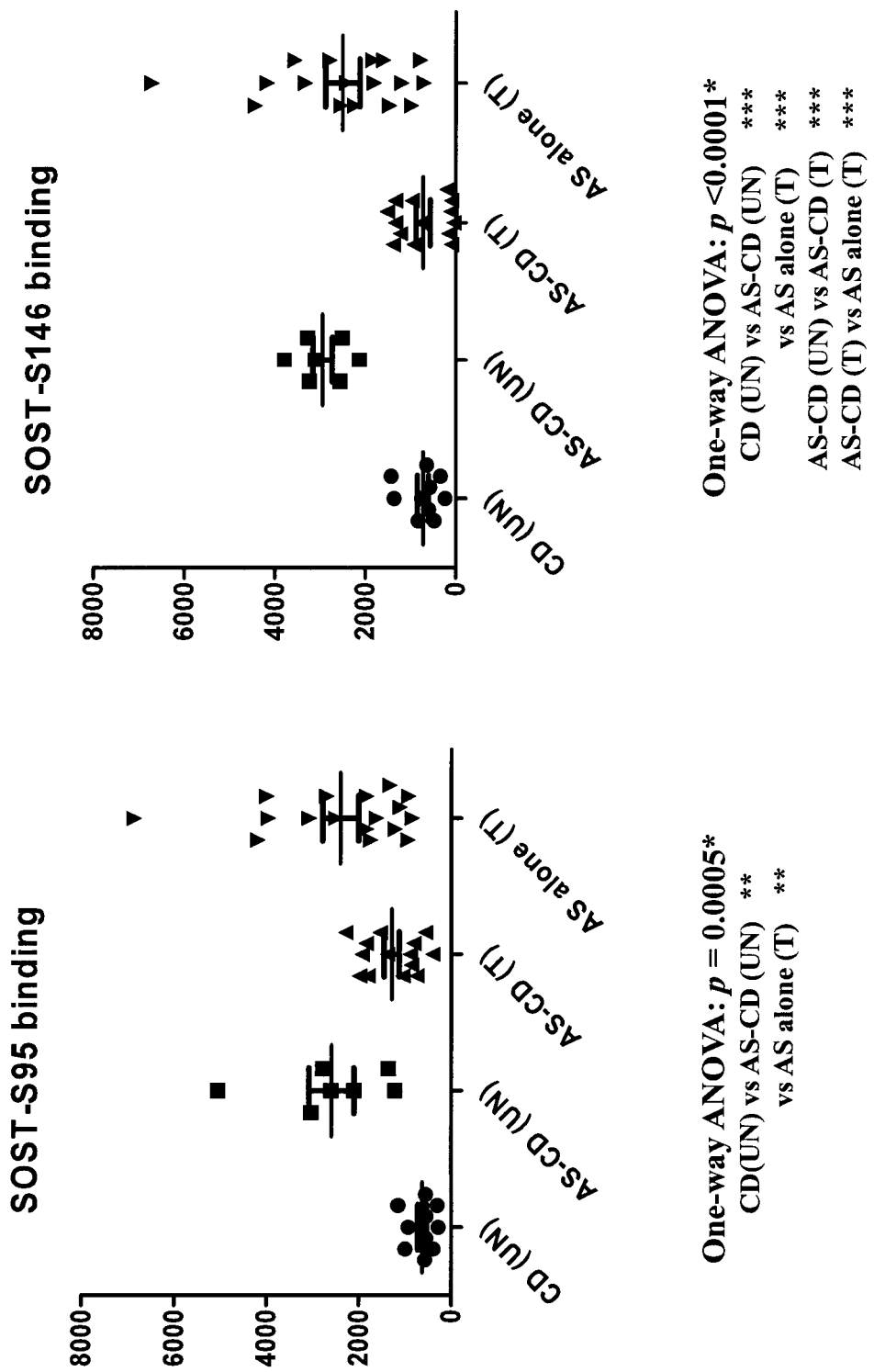

FIG. 9. Comparison of SOST-IgG IC levels in response to treatments. Graph on the left shows SOST-S95 binding and graph on the right shows SOST-S146 binding. Sera from 14 treated (T) and 7 untreated (UN) patients with AS-CD [AS-CD (UN) and AS-CD (T)] as well as 17 treated AS alone [AS alone (T)] were analyzed. IgG IC levels from 10 untreated CD alone [CD (UN)] patients were used as controls for comparison. Results were expressed as arbitrary units relative to the standard AS IgG in the total amount of IgG from 1 ml of each serum sample. The p-value of one-way ANOVA is shown below the graph.

and * denote significant p values between groups.

Figure 10:
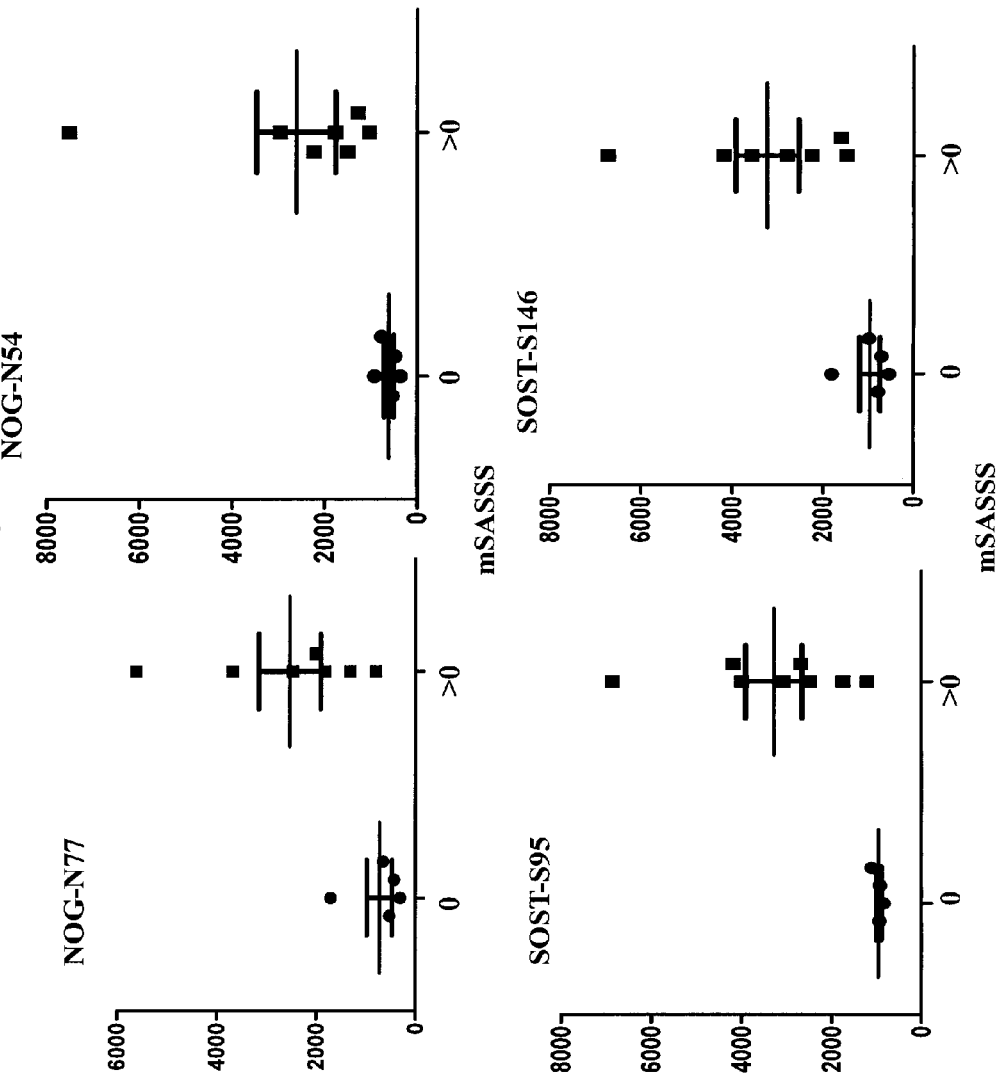

FIG. 10. Comparison of NOG- and SOST-IgG IC levels in AS alone patients with mSASSS of 0 vs >0. Results were expressed as arbitrary units relative to the standard AS IgG in the total amount of IgG from 1 ml of each serum sample. mSASSS denotes modified Stokes AS Spine Score.

Figure 11:
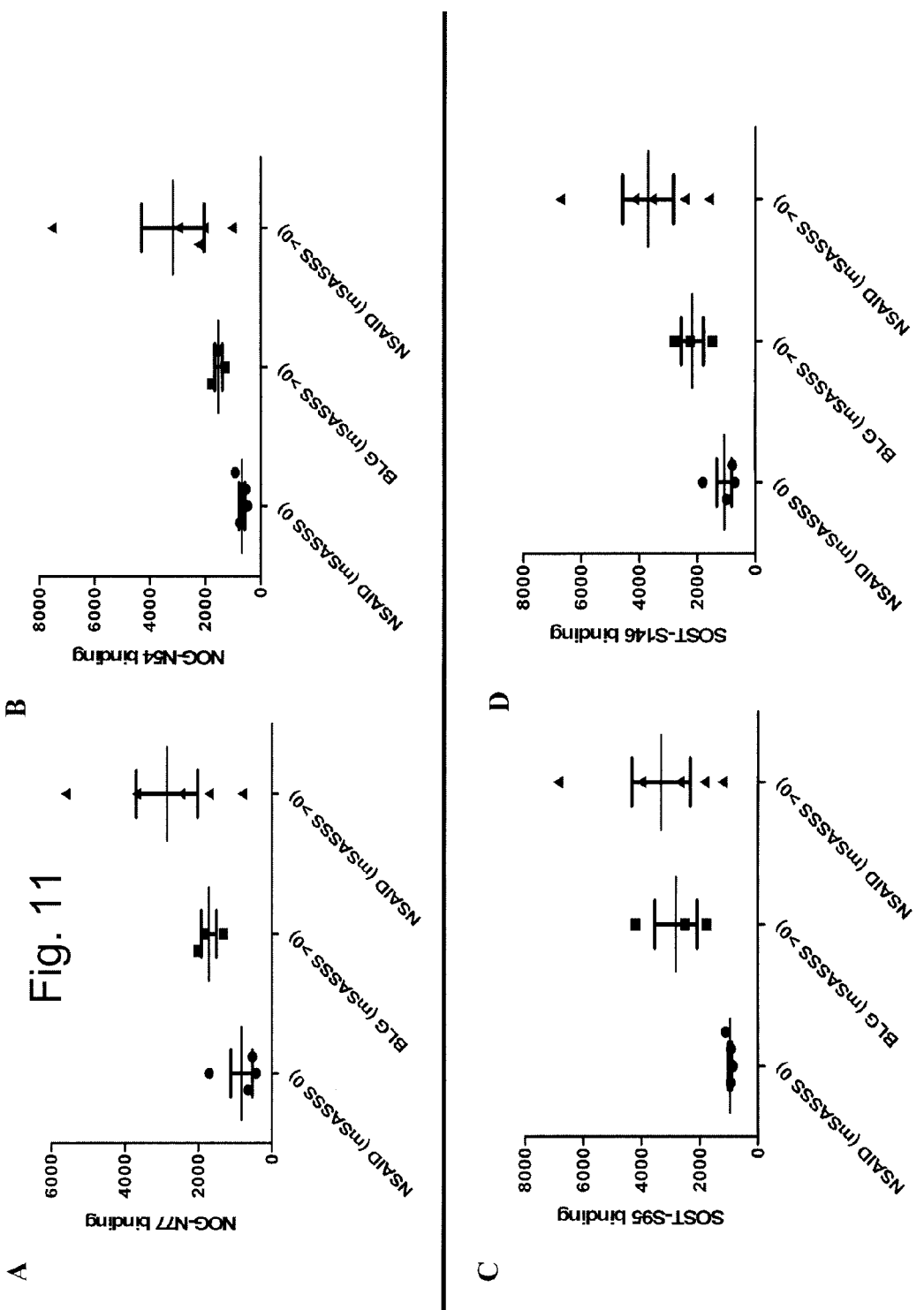

FIG. 11. Comparison of NOG- and SOST-IgG IC levels in NSAID- vs BLG-treated AS alone patients with mSASSS>0. Results were expressed as arbitrary units relative to the standard AS IgG in the total amount of IgG from 1 ml of each serum sample. mSASSS denotes modified Stokes AS Spine Score. NSAID denotes non-steroidal anti-inflammatory drugs; BLG denotes biologics; and mSASSS denotes modified Stokes AS Spine Score.

DETAILED DESCRIPTION

In the following description, numerous specific details are set forth to provide a thorough understanding of the invention. However, it is understood that the invention may be practiced without these specific details.

In an aspect, there is provided a method for categorizing a patient having inflammatory bowel disease as being at risk for developing ankylosing spondylitis, the method comprising: a. identifying a patient as having inflammatory bowel disease; b. determining a patient level of auto-antibodies directed against noggin (NOG) and/or sclerostin (SOST) in the patient; c. comparing said level to a control level representing normal individuals; and d. determining that the patient is at risk for developing ankylosing spondylitis if the patient level is higher than the control level.

The term "level" as used herein refers to a measurable level of a biomarker, for example, the level of proteins or portions thereof corresponding to the biomarker. In preferable embodiments, the level of autoantibodies is measured, for example, autoantibodies to NOG and SOST. A person skilled in the art would understand that levels of other products could also be measured, for example, the level of messenger RNA transcript expressed or of a specific exon or other portion of a transcript, the number or presence of DNA polymorphisms of the biomarkers, the enzymatic or other activities of the biomarkers, and the level of specific metabolites.

In addition, a person skilled in the art will appreciate that a number of methods can be used to determine the amount of a protein product of the biomarker of the invention, including immunoassays such as Western blots, ELISA, and immunoprecipitation followed by SDS-PAGE and immunocytochemistry.

As used herein, the term "control" refers to a specific value or dataset that can be used to prognose or classify the value e.g. level of autoantibodies obtained from the test sample associated with an outcome class. A person skilled in the art will appreciate that the comparison between the level of the biomarkers in the test sample and the level of the biomarkers in the control will depend on the control used.

In some embodiments, the level of autoantibodies in the sample compared to the control sample is at least 2× higher and can be 2-10× higher.

The term "sample" as used herein refers to any fluid, cell or tissue sample from a subject that can be assayed for biomarker expression products and/or a reference expression profile, e.g. genes differentially expressed in subjects.

In some embodiments, the patient has back pain.

In an aspect, there is provided a method of selecting treatment for a patient having inflammatory bowel disease; the method comprising the methods described herein for categorizing a patient having inflammatory bowel disease as being at risk for developing ankylosing spondylitis, further comprising selecting a treatment consistent with the treatment of both ankylosing spondylitis and inflammatory bowel disease, if the patient level of the auto-antibodies is higher than the control level.

In an embodiment, the treatment is an anti-TNF inhibitor, preferably infliximab, adalimumab, golimumab or certolizumab.

In an aspect, there is provided a method for categorizing a patient having ankylosing spondylitis as being at risk for developing inflammatory bowel disease, the method comprising: a. identifying a patient as having ankylosing spondylitis; b. determining a patient level of auto-antibodies directed against noggin (NOG) and/or sclerostin (SOST) in the patient; c. comparing said level to a control level representing normal individuals; d. determining that the patient is at risk for developing inflammatory bowel disease if the patient level is higher than the control level.

In an aspect, there is provided a method of determining the severity of ankylosing spondylitis in a patient not being treated for inflammatory bowel disease, comprising: a. determining a patient level of auto-antibodies directed against noggin (NOG) and/or sclerostin (SOST) in the patient; b. comparing said level to a control level representing normal individuals; c. determining the severity of ankylosing spondylitis, wherein the severity is related patient levels of the autoantibodies.

In an aspect, there is provided a method for monitoring treatment in a patient receiving treatment for ankylosing spondylitis, the method comprising: a. determining a patient level of auto-antibodies directed against noggin (NOG) and/or sclerostin (SOST) in the patient; b. comparing said level to a control level representing normal individuals; c. identifying a patient as being non-responsive to treatment if the patient level of auto-antibodies is higher than the control level and prior to treatment and does not decrease following or during treatment; wherein the auto-antibodies are directed against either at least part of a region comprising amino acids 73-102 of NOG or at least part of a region comprising amino acids 95-110 of SOST.

In an aspect, there is provided a method, performed by at least one computing device, for categorizing a patient having inflammatory bowel disease as being at risk for developing ankylosing spondylitis, the method comprising: a. determining, at a processor, a patient as having inflammatory bowel disease; b. determining, at a processor, a patient level of auto-antibodies directed against noggin (NOG) and/or sclerostin (SOST) in the patient; b. determining, at a processor, a control level representing normal individuals; c. determining, at a processor, whether the patient level is higher than the control level; d. determining, at a processor, that the patient is at risk for developing ankylosing spondylitis if the patient level is higher than the control level.

In an aspect, there is provided a system for categorizing a patient having inflammatory bowel disease as being at risk for developing ankylosing spondylitis, the system comprising: a non-transitory computer readable storage medium that stores computer-readable code; a processor operatively coupled to the non-transitory computer readable storage medium, the processor configured to implement the computer-readable code, the computer-readable code configured to: a. identify a patient as having inflammatory bowel disease; b. determine a patient level of auto-antibodies directed against noggin (NOG) and/or sclerostin (SOST) in the patient; c. compare said level to a control level representing normal individuals; d. determine that the patient is at risk for developing ankylosing spondylitis or inflammatory bowel disease if the patient level is higher than the control level.

In an aspect, there is provided a computer program product for use in conjunction with a computer having a processor and a memory connected to the processor, the computer program product comprising a computer readable storage medium having a computer mechanism encoded thereon, wherein the computer program mechanism may be loaded into the memory of the computer and cause the computer to carry out the methods described herein.

In some embodiments of all aspects, the auto-antibodies are directed against NOG, preferably against at least part of a region of NOG comprising amino acids 50-72 thereof (PD-PIFDPKEKDLNETLLRSLLGG—SEQ ID NO. 1); or amino acids 73-102 thereof (HYDPGFMATSPPEDRPGGGG-GAAGGAEDLA—SEQ ID NO. 2).

In some embodiments of all aspects, the auto-antibodies are directed against SOST, preferably against at least part of a region of SOST comprising amino acids 95-110 thereof (IGRGKWWRPSGPDFRC—SEQ ID NO. 3); or amino acids 146-158 thereof (TRFHNQSELKDFG—SEQ ID NO. 4).

The autoantibodies may be pre-complexed with antigen. For example, the detected autoantibody can be in a NOG-IgG immune complex, SOST-IgG immune complex or NOG/SOST-IgG immune complex.

In some embodiments of all aspects, the inflammatory bowel disease is Crohn's disease or ulcerative colitis.

Advantages of the present invention are further illustrated by the following examples. The examples and their particular details set forth herein are presented for illustration only and should not be construed as a limitation on the claims of the present invention.

EXAMPLES

Methods and Materials

Purification of Serum IgGs Free of Bound Antigens

IgGs were isolated from human sera using protein-G agarose (Pierce). IgGs adsorbed to protein-G beads were eluted with 0.1M glycine, pH2.7. To isolate IgGs free of NOG and SOST, the acidic eluates were transferred to Amicon® Ultracel 100K (Millipore) and spun for 10 min at 14,000 g in a microfuge. NOG monomer and SOST protein, with MWs of 26 and 24 Kd respectively, will pass through the filter device. The filters were inverted in microfuge tubes and spun for 2 min at 1,000 g to recover the retained materials containing IgG devoid of bound antigens (higher than 100K in MWs). Both the flow through and retained materials were neutralized with 1M phosphate pH8, aliquotted and stored at −70° C. until use.

Peptide Binding ELISAs

Peptides (Bio Basic Inc.) were generated with an amino-terminal cysteine residue to enable coupling of full length peptides to maleimide activated plates (Pierce). Excess maleimide groups were inactivated by cysteine-HCl. Antigen-free protein-G-purified IgG (1 µg/ml or less for higher titers) were incubated with HRP-anti-human IgG secondary antibody (Jackson) followed by HRP chromogenic substrates (Pierce) and read on an ELISA plate reader at 450 nm. Readings above background controls (without addition of human IgGs) were used for calculations. For normalization of results from different plates, a standard curve using serial dilutions of an AS patient IgG standard was included in each plate. Results were expressed as arbitrary units relative to the standard AS IgG present in the total amount of IgGs from 1 ml of each serum sample.

Peptides for Binding ELISAs
NOG:

```
N-54 (18aa)
FDPKEKDLNETLLRSLLG -       SEQ ID NO. 5

N-77 (13aa)
GFMATSPPEDRPG -            SEQ ID NO. 6
```

SOST

```
S-95 (15aa)
GRGKWWRPSGPDFRC -          SEQ ID NO. 7

S-146 (13aa)
TRFHNQSELKDFG -            SEQ ID NO. 8
```

Results and Discussion

Molecular Mimicry as a Potential Trigger of Autoimmunity to NOG/SOST in AS:

Potential Initiating NOG Epitope

Figure 1:
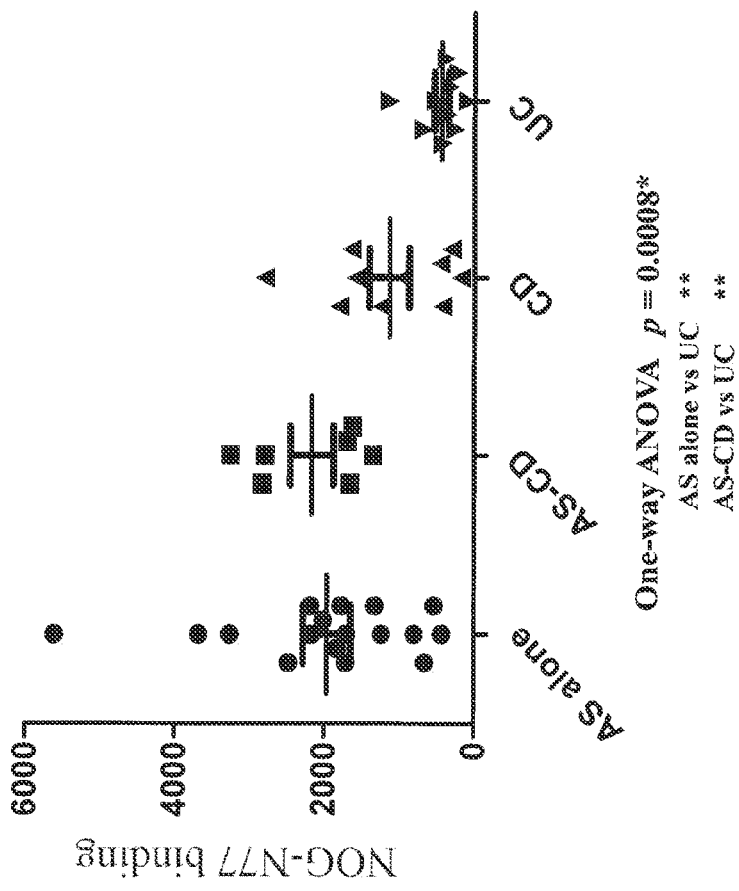
FIG. 1. Sequence homologies between bacterial antigens and a NOG peptide (NOG-N77) are shown in the top panel. Bottom panel: detection of human IgG which recognizes the NOG-N77 epitope. NOG-N77 binding ELISA was used to assay peptide-specific IgG in patients with ankylosing spondylitis alone (AS alone) (n=17), AS-CD (n=7), CD alone (n=10) and UC alone (n=10). Results were expressed as arbitrary units relative to the standard AS IgG in the total amount of IgG from 1 ml of each serum sample. ** denote significant p values between groups.

We recently showed that higher than normal levels of NOG-IgG immune complexes (ICs) are present in the sera of AS patients, especially those with coexisting AS and IBD (AS-IBD). Molecular mimicry, whereby an immune response is elicited by microbial antigens that have sequence homologies to host antigens, has long been viewed as a possible mechanism for the association of infection with autoimmune diseases. We have identified one NOG peptide (NOG-N77) containing the sequence MaTSPPEDRPG (SEQ ID NO. 10) with homologies to bacterial peptides from several bacterial species associated with arthritis (such as *Klebsiella*) and with IBD (such as *Mycobacterium* and *Ruminococccus*) (FIG. 1). We asked whether high levels of NOG-N77 IgG ICs are present in AS sera.

We developed a peptide-specific ELISA to detect ultrafiltration-generated IgG binding to NOG-N77 peptide. Compared to patients with ulcerative colitis alone (UC; n=10), AS-CD patients (n=7) and AS patients with no comorbidities ([AS alone]; n=17) had significantly higher serum levels of NOG-N77 IgG ICs (one way ANOVA: p=0.0008*; FIG. 1). Unexpectedly, some patients with CD alone (6 of 10) had elevated levels of NOG-N77 IgG ICs while all of them had normal levels of NOG-N54 IgG ICs (FIG. 2).

Figure 3:
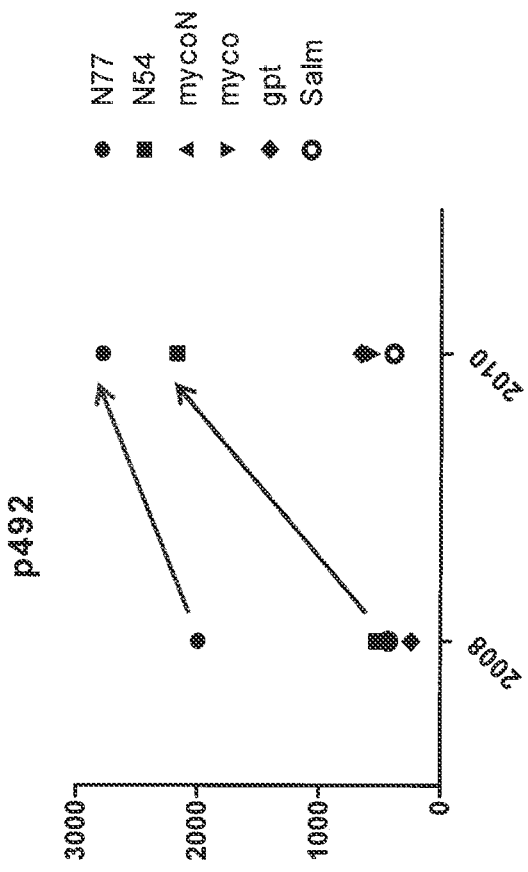
FIG. 3. Comparison of NOG-N77 (black circles) or NOG-N54 (red squares) IgG IC levels in sequentially obtained sera (taken in 2008 and 2010) from the same patient (p492). Reactivity to four different bacterial peptides (mycoN, myco, gpt and Salm) were used as specificity controls.

This unexpected result led us to the hypothesis that NOG-N77 is the initiating epitope of the autoimmune response to NOG, but development of articular symptoms would involve epitope spreading to a functionally relevant epitope such as NOG-N54. We showed previously that the interacting regions between NOG and SOST involve NOG-N54 and SOST-S146, and it has been shown that NOG-SOST complexes are inactive and mutually negating such that the normal antagonistic effect on BMP and Wnt/β-catenin signaling are neutralized. This postulated sequence of events was corroborated by serological results obtained from one initially CD alone patient (FIG. 3). This patient was diagnosed to have CD in 2002. He started to have back pain in 2005. His sera, taken in 2008, had elevated levels of NOG-N77, but normal levels of NOG-N54 IgG ICs concurrently. Two years later (2010), this patient had elevated levels of both NOG-N77 and NOG-N54 IgG ICs in the serum. Elevation of these NOG IgG ICs was correlated with higher levels of CRP (14 in 2010 and 5 in 2008). This patient was not taking NSAID, DMARD or BLG during these two years.

Potential Initiating SOST Epitope

Figure 4:
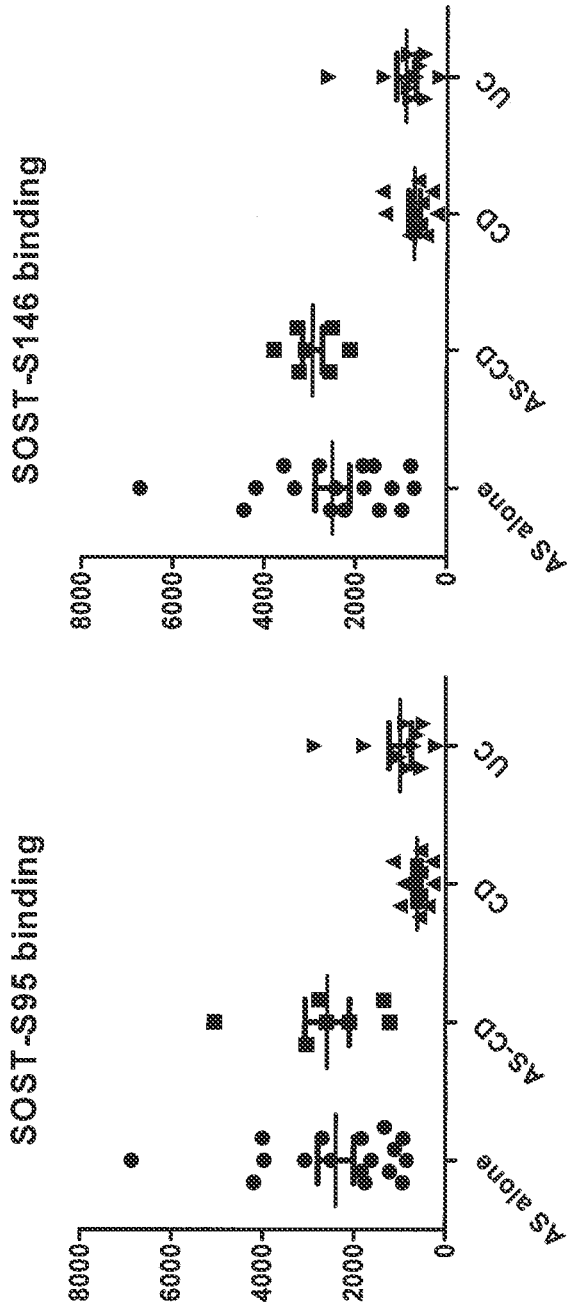
FIG. 4. Sequence homologies between bacterial antigens and a SOST peptide (SOST-S95) are shown in the top panel. Bottom panel: comparison of IgG levels recognizing either SOST-S95 (graph on the left) of SOST-S146 (graph on the right) in patients with AS alone (n=16), AS-CD (n=7), CD (n=10) and UC (n=10). Results were expressed as arbitrary units relative to the standard AS IgG in the total amount of IgG from 1 ml of each serum sample.

We also addressed whether there are any homologies between AS/IBD-associated bacterial antigens and the SOST protein. We identified one SOST peptide (SOST-S95; GRGKWWRPSGPDFRC) (SEQ ID NO. 13) with six amino acid homology (GKWWRP) (SEQ ID NO. 15) to a cell surface protein of *Clostridium difficile*. It is known that IBD patients are susceptible to *C. difficile* infection. The SOST-S95 peptide also has two regions of six amino acid homology each to alpha-L-fucosidase of *Sphingomonas* (or *Pseudomonas*; GRGKWW (SEQ ID NO. 16)) and to a DNA polymerase II alpha subunit of *Mycobacterium tuberculosis* (WRPSGP (SEQ ID NO. 17)) (FIG. 4). We thus asked whether high levels of SOST-S95 IgG ICs are present in AS sera.

We developed a peptide-specific ELISA to detect ultrafiltration-generated IgG binding to SOST-S95 peptide. Compared to patients with CD alone (n=10), AS-CD patients (n=7) and patients with AS alone (n=17) had significantly higher serum levels of SOST-S95 IgG ICs (one way ANOVA: p=0.0007; FIG. 4).

Figure 5:
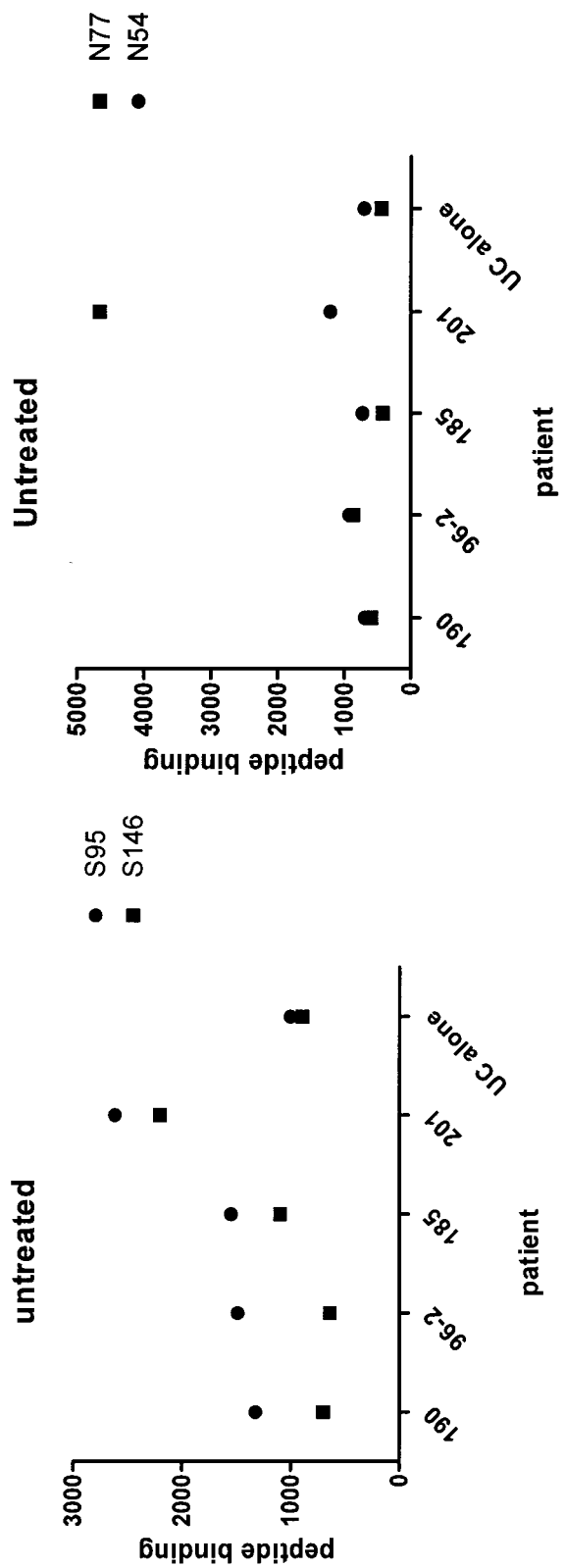
FIG. 5. Comparison of SOST-S95 and SOST-S146 IgG IC levels (graph on the left) or NOG-N77 and NOG-N54 IgG IC levels (graph on the right) in four untreated patients with concomitant anterior uveitis (190, 96-2, 185, 201). The mean levels of ICs from 10 UC patients serve as normal control values for comparison. Results were expressed as arbitrary units relative to the standard AS IgG in the total amount of IgG from 1 ml of each serum sample.

If SOST-S95 were the initiating SOST epitope, it is expected that reactivity to this epitope (SOST-S95) would temporally precede reactivity to other regions of the SOST protein (such as SOST-S146) in the evolution of the disease process. In four untreated AS patients with concomitant anterior uveitis (AS-AAU), elevated SOST-S95 IgG ICs were detected in their sera. However, at the same point in time, the levels of SOST-S146 IgG ICs were within the normal range in three out of four of these sera. In the serum from patient 201, in addition to elevated levels of SOST-S95 and SOST-S146 IgG ICs, significantly higher levels of NOG-N77 IgG ICs were also detected (FIG. 5). UC alone patients (the mean levels of 10 patients were shown in FIG. 5) had normal levels of these ICs.

Changes of NOG IgG IC Levels in Response to Treatment in AS-CD Patients

Figure 6:
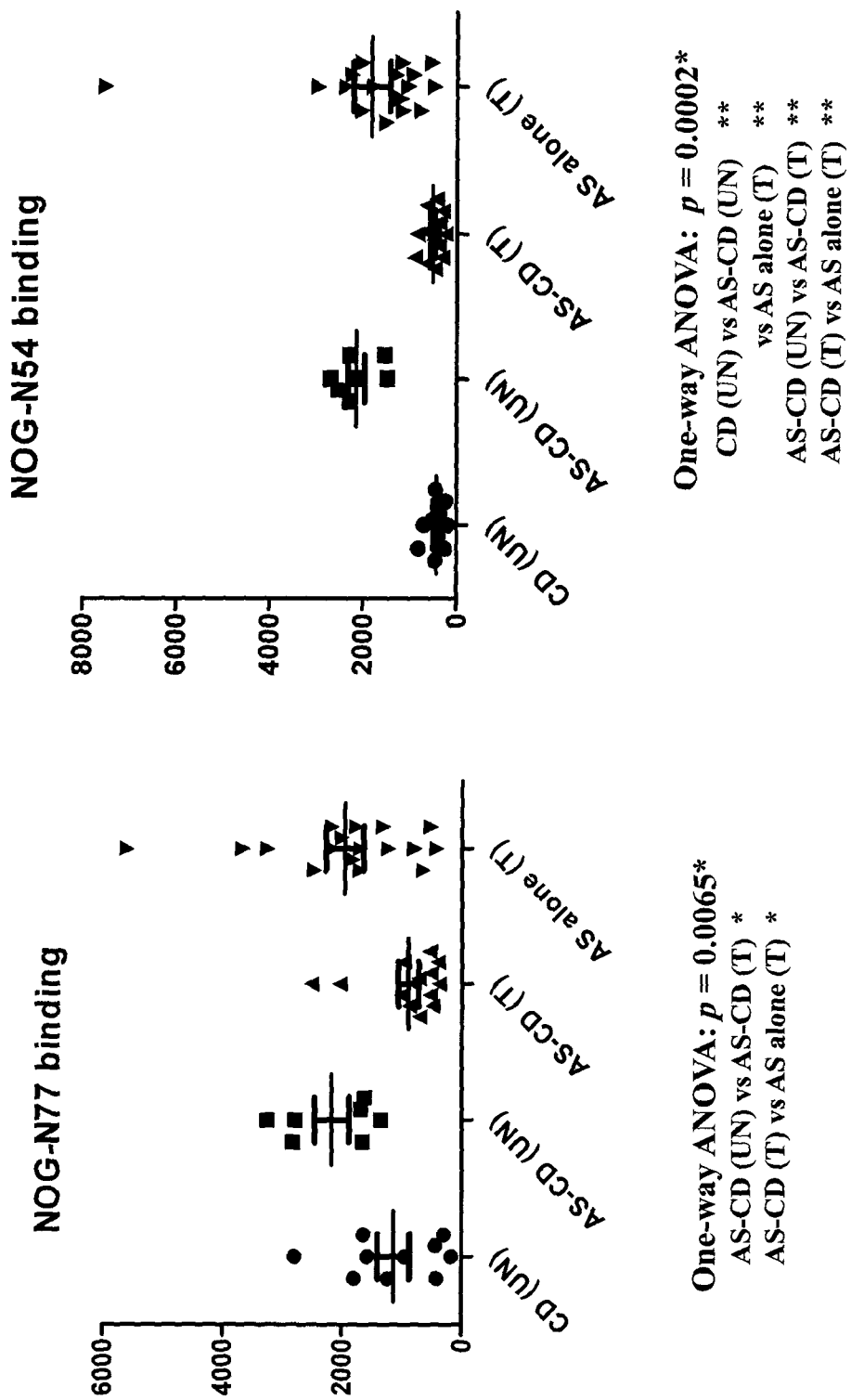
FIG. 6. Comparison of NOG-IgG IC levels in response to treatments. Graph on the left shows NOG-N77 binding and graph on the right shows NOG-N54 binding. Sera from 14 treated (T) and 7 untreated (UN) patients with AS-CD [AS-CD (UN) and AS-CD (T)] as well as 17 treated AS alone [AS alone (T)] were analyzed. IgG IC levels from 10 untreated CD alone [CD (UN)] patients were used as controls for comparison. Results were expressed as arbitrary units relative to the standard AS IgG in the total amount of IgG from 1 ml of each serum sample. The p-value of one-way ANOVA is shown below the graph.

Untreated AS-CD patients had higher than normal levels of NOG-N77 and NOG-N54 IgG ICs respectively (FIG. 6). But in AS-CD patients receiving medications (NSAID or BLG), there was a significant decrease in serum levels of these IgG ICs (FIG. 6). Two AS-CD patients (130-2 and 619-2) treated with BLG showed a different profile of NOG IgG IC levels: both had elevated levels of NOG-N77, but normal levels of NOG-N54 IgG ICs respectively (FIG. 7). Both patients had BLG treatment for 1-2 years prior to this serum sampling and were considered as non-responders to BLG treatments. This result implicates that reactivity to the initiating NOG epitope (NOG-N77) is sustained by cross-reacting bacterial antigens, even though BLG treatment manages to suppress the functionally relevant NOG-N54 IgG IC levels. In contrast, another AS-CD patient (17-2) had elevated levels of both NOG-N77 and NOG-N54 IgG ICs before treatment with BLG, but both NOG IgG IC levels fell to below normal levels after BLG treatment. The suppression of NOG IgG IC levels in this patient serum was correlated with a drop of CRP levels from 55 to normal level (3) after BLG treatment, implicating a more successful treatment response to BLG therapy in this AS-CD patient.

Analysis of the sequential samples from six AS-CD patients showed that levels of both NOG-N77 and NOG-N54 IgG ICs fell to below normal levels after treatments. The treatment response correlates with a drop in another inflammatory marker (CRP) and with symptomatic improvement of AS activity as measured by BASDAI (FIG. 8). These results suggest that the NOG IgG ICs are relevant to disease activity.

Differential Changes of SOST IgG ICs in Response to Treatment in AS-CD Patients

In view of our results showing that treated AS-CD patients had a significant decrease in the levels of NOG IgG ICs, we asked whether these treated AS-CD patients also had suppressed levels of SOST IgG ICs. Although there was a trend of decreased levels of SOST-S95 IgG ICs in treated AS-CD patients (n=14), the levels were not significantly different from those from the untreated AS-CD patients (n=7) (FIG. 9). This result implicates that either reactivity to SOST-S95 persisted due to the presence of bacterial antigens and/or the current treatment is not effective in dampening this immune response.

NOG/SOST IgG IC Levels Correlate with Ankylosis Severity in Patients with AS Alone Radiographic changes of the spine (cervical and lumbar) in AS patients are scored using the modified Stokes AS Spine Score (mSASSS) and the scores obtained reflect on the severity of ankylosis. We asked whether NOG/SOST IgG IC levels can serve as biomarkers for ankylosis severity. Ultrafiltration-generated IgG from patients with AS alone were analyzed for binding to NOG-N77, NOG-N54, SOST-S95 and SOST-146 peptides. Five of the patients had mSASSS of 0 and seven of them had mSASSS of >0. In all cases, patients with mSASSS of >0 had significantly higher levels of NOG/SOST IgG IC levels (FIG. 10).

NOG/SOST IgG IC Levels are Associated with Treatments in Patients with AS Alone

Unlike AS-CD patients, most patients with AS alone remained having elevated levels of NOG/SOST IgG ICs even after treatments (NSAID or BLG). We asked whether NSAID and BLG had differential effects on NOG/SOST IgG IC levels. We analyzed sera from four patients with mSASSS 0 who were taking NSAID. This group of patients had normal levels of NOG/SOST IgG IC levels (FIG. 11). We also analyzed sera from eight patients with mSASSS>0. Three of them were treated with BLG and five of them were treated with NSAID. Compared to the NSAID treated patients, the BLG treated patients in this group had lower levels of NOG-N77, NOG-N54 and SOST-S146 IgG ICs (FIGS. 11A, B and D). This result suggested that BLG treatment appears to be more effective in suppressing the levels of these IgG ICs. However, these ICs remained at higher than normal levels. Intriguingly, both NSAID and BLG treatments appeared to be less effective in lowering the levels of SOST-S95 IgG ICs in patients with AS alone and mSASSS>0 (FIG. 11C). Taken together, it appears that BLG treatment is more effective in lowering the functionally relevant (NOG-N54 and SOST-S146) IgG ICs in patients with AS alone and mSASSS>0.

Although preferred embodiments of the invention have been described herein, it will be understood by those skilled in the art that variations may be made thereto without departing from the spirit of the invention or the scope of the appended claims. All documents disclosed herein are incorporated by reference.

The invention claimed is:

1. A method for categorizing a patient having inflammatory bowel disease as being at risk for developing ankylosing spondylitis, the method comprising:
   a. identifying a patient as having inflammatory bowel disease;
   b. determining a patient level of auto-antibodies directed against noggin (NOG) and/or sclerostin (SOST) in the patient;
   c. comparing said level to a control level representing normal individuals;
   d. determining that the patient is at risk for developing ankylosing spondylitis if the patient level is higher than the control level.

2. The method of claim 1, wherein the auto-antibodies are directed against NOG.

3. The method of claim 2, wherein the auto-antibodies are directed against at least part of a region of NOG comprising amino acids 50-72 thereof (PDPIFDPKEKDLNETLL-RSLLGG—SEQ. ID NO. 1).

4. The method of claim 2, wherein the auto-antibodies are directed against at least part of a region of NOG comprising amino acids 73-102 thereof (HYDPGF-MATSPPEDRPGGGGGAAGGAEDLA—SEQ. ID NO. 2).

5. The method of claim 1, wherein the auto-antibodies are directed against SOST.

6. The method of claim 5, wherein the auto-antibodies are directed against at least part of a region of SOST comprising amino acids 95-110 thereof (IGRGKWWRPSGPDFRC—SEQ. ID NO. 3).

7. The method of claim 5, wherein the auto-antibodies are directed against at least part of a region of SOST comprising amino acids 146-158 thereof (TRFHNQSELKDFG—SEQ. ID NO. 4).

8. The method of claim 1, wherein the patient has back pain.

9. The method of claim 1, wherein the inflammatory bowel disease is Crohn's disease or ulcerative colitis.

10. A method of selecting treatment for a patient having inflammatory bowel disease; the method comprising the method of claim 1, further comprising selecting a treatment consistent with the treatment of both ankylosing spondylitis and inflammatory bowel disease, if the patient level of the auto-antibodies is higher than the control level.

11. The method of claim 10, wherein the treatment is an anti-TNF inhibitor, preferably infliximab, adalimumab, golimumab or certolizumab.

* * * * *

```
                        SEQUENCE LISTING

<160> NUMBER OF SEQ ID NOS: 18

<210> SEQ ID NO 1
<211> LENGTH: 23
<212> TYPE: PRT
<213> ORGANISM: Homo sapiens

<400> SEQUENCE: 1

Pro Asp Pro Ile Phe Asp Pro Lys Glu Lys Asp Leu Asn Glu Thr Leu
1               5                   10                  15

Leu Arg Ser Leu Leu Gly Gly
            20

<210> SEQ ID NO 2
<211> LENGTH: 30
<212> TYPE: PRT
<213> ORGANISM: Homo sapiens

<400> SEQUENCE: 2

His Tyr Asp Pro Gly Phe Met Ala Thr Ser Pro Pro Glu Asp Arg Pro
1               5                   10                  15

Gly Gly Gly Gly Gly Ala Ala Gly Gly Ala Glu Asp Leu Ala
            20                  25                  30

<210> SEQ ID NO 3
<211> LENGTH: 16
<212> TYPE: PRT
<213> ORGANISM: Homo sapiens

<400> SEQUENCE: 3

Ile Gly Arg Gly Lys Trp Trp Arg Pro Ser Gly Pro Asp Phe Arg Cys
1               5                   10                  15

<210> SEQ ID NO 4
<211> LENGTH: 13
<212> TYPE: PRT
<213> ORGANISM: Homo sapiens

<400> SEQUENCE: 4

Thr Arg Phe His Asn Gln Ser Glu Leu Lys Asp Phe Gly
1               5                   10

<210> SEQ ID NO 5
<211> LENGTH: 18
<212> TYPE: PRT
<213> ORGANISM: Homo sapiens

<400> SEQUENCE: 5

Phe Asp Pro Lys Glu Lys Asp Leu Asn Glu Thr Leu Leu Arg Ser Leu
1               5                   10                  15

Leu Gly

<210> SEQ ID NO 6
<211> LENGTH: 13
<212> TYPE: PRT
<213> ORGANISM: Homo sapiens
```

```
<400> SEQUENCE: 6

Gly Phe Met Ala Thr Ser Pro Pro Glu Asp Arg Pro Gly
1               5                   10

<210> SEQ ID NO 7
<211> LENGTH: 15
<212> TYPE: PRT
<213> ORGANISM: Homo sapiens

<400> SEQUENCE: 7

Gly Arg Gly Lys Trp Trp Arg Pro Ser Gly Pro Asp Phe Arg Cys
1               5                   10                  15

<210> SEQ ID NO 8
<211> LENGTH: 13
<212> TYPE: PRT
<213> ORGANISM: Homo sapiens

<400> SEQUENCE: 8

Thr Arg Phe His Asn Gln Ser Glu Leu Lys Asp Phe Gly
1               5                   10

<210> SEQ ID NO 9
<211> LENGTH: 44
<212> TYPE: PRT
<213> ORGANISM: Homo sapiens

<400> SEQUENCE: 9

Pro Asp Pro Ile Phe Asp Pro Lys Glu Lys Asp Leu Asn Glu Thr Leu
1               5                   10                  15

Leu Arg Ser Leu Leu Gly Gly His Tyr Asp Pro Gly Phe Met Ala Thr
                20                  25                  30

Ser Pro Pro Glu Asp Arg Pro Gly Gly Gly Gly
                35                  40

<210> SEQ ID NO 10
<211> LENGTH: 11
<212> TYPE: PRT
<213> ORGANISM: Mycobacterium

<400> SEQUENCE: 10

Met Thr Thr Ile Pro Pro Glu Asp Ile Pro Gly
1               5                   10

<210> SEQ ID NO 11
<211> LENGTH: 7
<212> TYPE: PRT
<213> ORGANISM: Akkermansia muciniphila

<400> SEQUENCE: 11

Pro Pro Glu Asp Arg Pro Gly
1               5

<210> SEQ ID NO 12
<211> LENGTH: 8
<212> TYPE: PRT
<213> ORGANISM: Klebsiella

<400> SEQUENCE: 12

Ser Pro Pro Glu Asp Arg Arg Gly
1               5
```

```
<210> SEQ ID NO 13
<211> LENGTH: 15
<212> TYPE: PRT
<213> ORGANISM: Homo sapiens

<400> SEQUENCE: 13

Gly Arg Gly Lys Trp Trp Arg Pro Ser Gly Pro Asp Phe Arg Cys
1               5                   10                  15

<210> SEQ ID NO 14
<211> LENGTH: 16
<212> TYPE: PRT
<213> ORGANISM: Homo sapiens

<400> SEQUENCE: 14

Thr Arg Phe His Asn Gln Ser Glu Leu Lys Asp Phe Gly Pro Glu Thr
1               5                   10                  15

<210> SEQ ID NO 15
<211> LENGTH: 6
<212> TYPE: PRT
<213> ORGANISM: C. Difficile

<400> SEQUENCE: 15

Gly Lys Trp Trp Arg Pro
1               5

<210> SEQ ID NO 16
<211> LENGTH: 6
<212> TYPE: PRT
<213> ORGANISM: Sphingomonas

<400> SEQUENCE: 16

Gly Arg Gly Lys Trp Trp
1               5

<210> SEQ ID NO 17
<211> LENGTH: 6
<212> TYPE: PRT
<213> ORGANISM: Mycobacterium tuberculosis

<400> SEQUENCE: 17

Trp Arg Pro Ser Gly Pro
1               5

<210> SEQ ID NO 18
<211> LENGTH: 8
<212> TYPE: PRT
<213> ORGANISM: Klebsiella pneumoniae

<400> SEQUENCE: 18

Lys Trp Trp Lys Pro Asp Gly Pro
1               5
```